(12) United States Patent
Shih et al.

(10) Patent No.: US 6,673,286 B2
(45) Date of Patent: Jan. 6, 2004

(54) METHOD OF MAKING POROUS BIODEGRADABLE POLYMERS

(75) Inventors: Hsi-Hsin Shih, Taichung (TW);
Kuang-Rong Lee, Hsinchu (TW);
Huey-Min Lai, Hsinchu (TW);
Chin-Chin Tsai, Taichung (TW);
Yuan-Chia Chang, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 175 days.

(21) Appl. No.: 09/947,182

(22) Filed: Sep. 4, 2001

(65) Prior Publication Data

US 2003/0064156 A1 Apr. 3, 2003

(30) Foreign Application Priority Data

Aug. 3, 2001 (TW) ........................................ 90118983 A

(51) Int. Cl.[7] ............................................. B29C 44/02
(52) U.S. Cl. ........................ 264/50; 264/53; 521/84.1; 521/94; 521/97
(58) Field of Search ............................... 264/50, 51, 53; 521/84.1, 94, 97

(56) References Cited

U.S. PATENT DOCUMENTS 5,494,940 A * 2/1996 Unger et al. .................. 521/66

FOREIGN PATENT DOCUMENTS

WO         WO 91/09079         * 6/1991

* cited by examiner

Primary Examiner—Allan R. Kuhns
(74) Attorney, Agent, or Firm—Darby & Darby

(57) ABSTRACT

A method of making a porous biodegradable polymer is disclosed, which comprises (a) placing a biodegradable polymer and a solvent in a chamber; (b) adding a supercritical fluid to the chamber and maintaining the chamber at a predetermined temperature for a sufficient period of time to allow the supercritical fluid to dissolve into the biodegradable polymer with the help of the solvent; and (c) venting the supercritical fluid and the solvent by reducing the pressure in the chamber, thereby obtaining a porous biodegradable polymer.

16 Claims, 1 Drawing Sheet

METHOD OF MAKING POROUS BIODEGRADABLE POLYMERS

BACKGROUND OF THE INVENTION

1. Field of the Invention

The present invention relates in general to a method of making porous materials. More particularly, it relates to a method of making porous biodegradable polymers.

2. Description of the Related Arts

Polymeric materials which are both porous and biodegradable are useful in a variety of pharmaceutical applications, such as controlled-release drug delivery systems and surgical implantation. Four major techniques are employed in making porous biodegradable materials: (1) solvent casting/salts leaching; (2) freeze drying (phase separation); (3) emulsion freeze drying; and (4) gas foaming. The first three techniques require excessive quantities of solvent, complicated process, and the operating time is undesirably long. In the last technique, gas forming, a biodegradable polymer is brought into contact with a high-pressure fluid such as $CO_2$ or $N_2$, followed by reducing the pressure in a sharp step to generate void spaces inside a bulk polymer. However, polymers which contain protein structures and hydrogen bonds such as gelatin and collagen are hydrophilic, and it is not easy for the hydrophobic fluid (such as $CO_2$) to permeate into these polymer matrices. Therefore, in the current state of the art, the gas foaming technique cannot produce hydrophilic porous materials effectively.

World Patent Application No. WO91/09079 issued to D. P., Roberto et al., discloses a method of preparing a biodegradable porous matrix, which comprises contacting a biodegradable polymer with supercritical carbon dioxide in a chamber and subsequently reducing the pressure in the chamber in a sharp step. A porous spongy material such as poly(glycolic acid) (PGA) or poly(lactide glycolide acid) (PLGA) carrying an active ingredient can be obtained.

As described in *J. Biomed. Mater. Res.*, 42, 396 (1998) issued to Harris et al., the supercritical $CO_2$ foaming technique cannot directly lead to opened-cell morphology. A method combining supercritical $CO_2$ foaming and leaching techniques is therefore proposed in this article to achieve open-celled biodegradable materials. This method is limited, however, to water-insoluble polymers such as PLGA.

*J. Controlled Release*, 66, 177–185 (2000) issued to Hill et al., discloses a method in which a PLGA polymer support comprising a protein is prepared by forming an emulsion of PLGA and the protein, placing the emulsion in a high pressure chamber, and then reducing the pressure in the chamber in a sharp step.

*J. Biomed. Mater. Res.*, 14, 511 (1980) issued to Dagalakis et al., discloses a method of drying porous collagen by supercritical $CO_2$, in which the solvent in a collagen solution is first replaced by ethanol, and the ethanol is then removed by supercritical $CO_2$ extraction. This method requires excessive quantities of solvent and ethanol, and therefore is economically disadvantageous.

SUMMARY OF THE INVENTION

An object of the invention is to provide a method of making porous biodegradable polymers, by which hydrophilic polymers can be foamed in an effective and controllable manner.

To obtain the above object, the present method is characterized by adopting solvent in supercritical fluid processing to help the hydrophobic supercritical fluid to penetrate into hydrophilic polymer, and finally dissolve into the polymer.

The method according to the invention comprises the steps of: (a) placing a biodegradable polymer and a solvent in a chamber; (b) adding a supercritical fluid to the chamber and maintaining the chamber at a predetermined temperature for a sufficient period of time to allow the supercritical fluid to dissolve into the biodegradable polymer with the help of the solvent; (c) venting the supercritical fluid and the solvent by reducing the pressure in the chamber, thereby obtaining the porous biodegradable polymer; and optionally (d) promptly heating the porous biodegradable polymer to increase the porosity thereof.

With the present method, the use of excessive organic solvent can be avoided and the operating time can be reduced. Further, the pore size and morphology of the porous material can be controlled by adjusting the operating pressure and temperature.

DETAILED DESCRIPTION OF THE INVENTION

By supercritical fluid is meant a gas or liquid above its critical point. At the critical point, physical properties of the liquid and gaseous states, in particular the densities, are identical. The temperature and pressure values at the critical point may be termed the critical conditions and are constant for a given fluid. Any supercritical fluid, including carbon dioxide, lower hydrocarbons (hydrocarbons that contain 1 to 8 carbon atoms), refrigerant, nitrogen, and ammonia, may be used in the method of the present invention. Carbon dioxide ($CO_2$), at a pressure of at least 7376 kPa and a temperature of at least 31.1° C., is a preferred example.

In operation, the biodegradable polymer is placed in a high pressure chamber or any appropriate device, along with a solvent. After setting the operating temperature, fluid from a cylinder is passed through a pump, which raises the pressure, and then fed into the chamber where it is heated above its critical temperature. Given sufficient time, the supercritical fluid will dissolve into the polymer with the help of the solvent. Thereafter, the pressure inside the chamber is reduced in a sharp step. The sharp pressure reduction contributes towards achieving the desired porosity in the material obtained, and the solvent dissolved in the supercritical fluid can be removed at the same time.

The present method is particularly suited for preparing hydrophilic porous polymers such as gelatin or collagen, but may be used to make hydrophobic porous polymers.

To help hydrophobic fluid (such as $CO_2$) dissolve into the hydrophilic polymer, as a key aspect of the invention, a suitable solvent is placed in the high pressure chamber in addition to the biodegradable polymer. The solvent used herein should be able to dissolve the biodegradable polymer to form a single phase, so that it can help the supercritical fluid to dissolve into the polymer. For hydrophilic biodegradable polymers, suitable solvents include diluted acidic solutions, diluted basic solutions, neutral (slat) solutions, solvents that are miscible with water (such as alcohols), or mixtures thereof. The amount of the solvent can be adjusted to modify the porosity of the porous biodegradable polymer. The greater the amount of solvent employed, the higher the porosity of the resulting product, but the longer the time needed for drying the product.

After placing the solvent and the polymer in the chamber, a supercritical fluid is fed into the chamber through a high pressure pump. The chamber is maintained at a predetermined temperature for a sufficient time to allow the supercritical fluid to permeate the biodegradable polymer with the help of the solvent, and finally dissolve the polymer. Thus, a single-phase fluid is formed with the polymer-solvent mixture. The operating time and temperature can also be adjusted to modify the product porosity. The higher the operating temperature of the chamber or the longer the operating time, the higher the porosity achieved. When carbon dioxide is employed as the supercritical fluid, the operating temperature is preferably between about 40° to 150° C., the operating time is preferably between about 5 minutes and 6 hours, and the pressure inside the chamber must be greater than ambient pressure, at about 101.325 kPa (1 atmosphere).

Once this process is complete, the pressure inside the chamber is reduced to a value below the critical pressure of the fluid in a sharp step, typically in a period from 0.1 to 10 seconds. In one embodiment of the invention, the pressure in the chamber is reduced to ambient pressure in the sharp step. The sharp pressure reduction contributes towards achieving the desired porosity in the material obtained, and the solvent dissolved in the supercritical fluid can be removed thereby. However, if the resulting product is found to be moist, it may be desirable to remove the solvent by continuously purging the chamber with the fluid, or by increasing the operating time or temperature.

The morphology of the porous material thus obtained is generally closed-celled. The porous polymeric product may have a porosity of about 89% to 98% with closed pores between about 50 and 250 $\mu$m in diameter. The porous biodegradable polymers with closed-cell morphology are useful in controlled-release drug delivery systems.

If interconnected pores are desirable, the porous product obtained from the pressure reduction step is promptly heated to an elevated temperature in an oven. This heating accelerates the evaporation of the fluid contained in the porous material. The porosity is increased, and the pore spaces are interconnected to form open cell morphology as a result. The heating step is preferably carried out under conditions of about 150° to 250° C. for about 1 to 20 seconds. A highly porous product with a porosity of about 97% to 99% and with interconnected pores between about 50 and 250 $\mu$m in diameter can be achieved. The porous biodegradable polymers with open-cell morphology are useful in a variety of tissue engineering applications, such as three-dimensional scaffolds for cell culture or media for cell and tissue culture, to form artificial skins, burn wound coverings, haemostasis, and so on.

BRIEF DESCRIPTION OF THE DRAWINGS

The above and other objects, features, and advantages of the present invention will become apparent from the following detailed description of preferred embodiments of the invention explained with reference to the accompanying drawings, in which.

EXAMPLE 1

A 2 cm×2 cm gelatin and a 0.01 M acetic acid solution were loaded in a high pressure chamber with a weight ratio of 1:1. $CO_2$ was applied at a fixed pressure of 4000 psi, but the operating temperature and time were varied, as listed in Table 1.

The $CO_2$ was taken from a cylinder and loaded into the high pressure chamber. The pressure of 4000 psi was applied by means of a high pressure pump (Sera, C/RF 110-500). The temperature was kept constant at 60° C., 80° C., 100° C., and 120° C., respectively during the process. After 1 or 2 hours the pressure was reduced to ambient pressure in a sharp step. The chamber was opened and a porous material was obtained.

Figure 1:
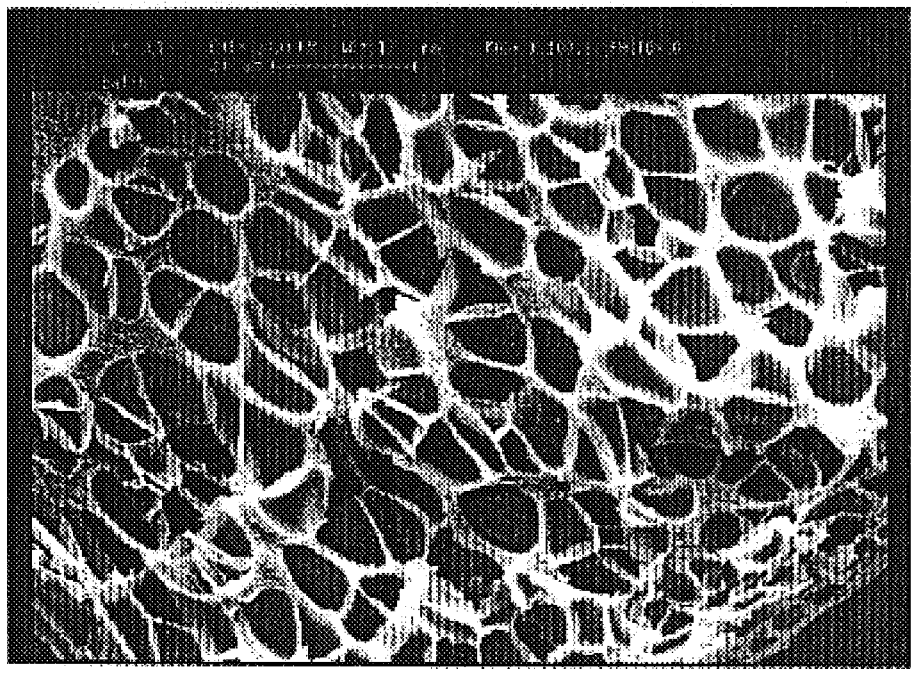
FIG. 1 is a scanning electron micrograph (SEM) of a sample obtained in Example 1, which shows closed cell morphology.

The porosity (P) of the material may be calculated, in percentage terms, using the following equation:

$$P=[1-(D1/D2)]\times 100$$

in which D1 is the apparent density of the product and D2 is the true density, measured using a MP-200S electric dencimeter. The operating conditions and porosities of the materials obtained are summarized in Table 1. The morphology and pore size of the porous material were determined using scanning electron microscope (SEM). FIG. 1, which is a SEM photograph of sample 3, shows that the pores are generally closed-celled, and the pore size is between about 80 to 120 $\mu$m.

TABLE 1

| Sample | Pressure (psi) | Temperature (° C.) | Time (hr) | Porosity (%) |
|---|---|---|---|---|
| 1 | 4000 | 60 | 1 | — |
| 2 | 4000 | 80 | 1 | 89.5 |
| 3 | 4000 | 100 | 1 | 89.3 |
| 4 | 4000 | 120 | 1 | 97.1 |
| 5 | 4000 | 100 | 2 | 97.5 |

EXAMPLE 2

The procedure outlined in Example 1 was repeated, but the gelatin and the acetic acid solution were loaded with varying weight ratios as indicated in Table 2. The results in Table 2 show that the porosity increases with the amount of solvent employed, but a longer time is needed for drying the product.

TABLE 2

| Sample | Gelatin:Solvent (w/w) | Pressure (psi) | Temperature (° C.) | Time (hr) | Porosity (%) |
|---|---|---|---|---|---|
| 4 | 1:1 | 4000 | 120 | 1 | 97.1 |
| 6 | 1:1.5 | 4000 | 120 | 1 | 89.1 |
| 7 | 1:2 | 4000 | 120 | 1 | — |
| 8 | 1:2 | 4000 | 120 | 2 | 98.1 |
| 9 | 1:3 | 4000 | 100 | 2 | — |

EXAMPLE 3

Figure 2:
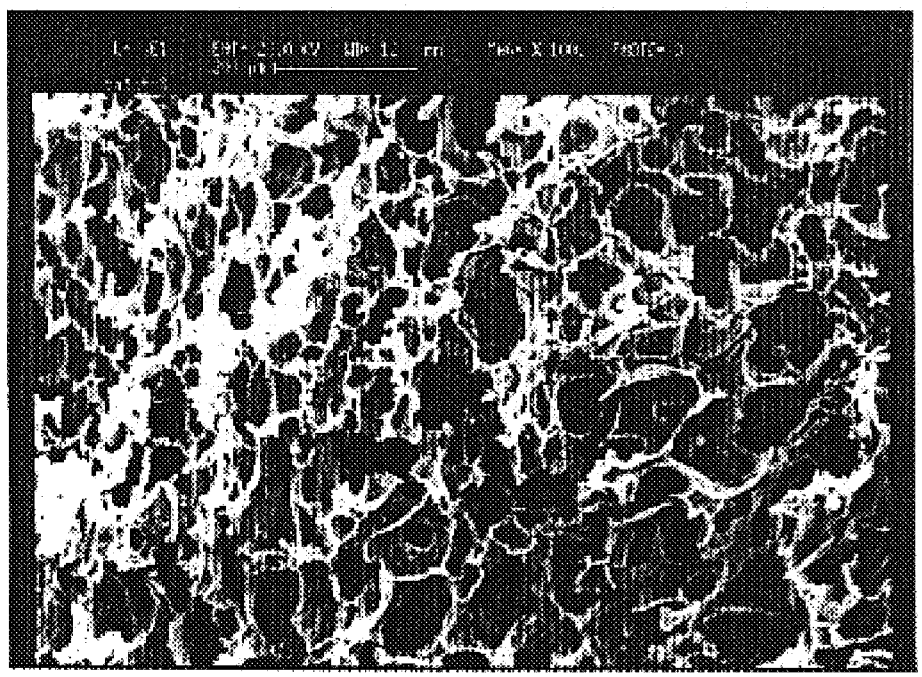
FIG. 2 is a scanning electron micrograph (SEM) of a sample obtained in Example 3, which shows open cell morphology.

The porous materials obtained in the Examples 1–2 were placed in a 200° C. oven for 10 seconds promptly after the pressure reduction step. The results in Table 3 show that a higher porosity was achieved due to the rapid evaporation of $CO_2$. Additionally, the SEM photograph of FIG. 2 reveals that the pores are interconnected.

TABLE 2

| Sample | Porosity (%) | |
| --- | --- | --- |
| | Before 200° C. heating | After 200° C. heating |
| 1 | — | — |
| 2 | 89.5 | 97.1 |
| 3 | 89.3 | 97.9 |
| 4 | 97.1 | 98.5 |
| 5 | 97.5 | 97.9 |
| 6 | 98.1 | 98.7 |
| 7 | — | — |
| 8 | 98.1 | 98.4 |
| 9 | — | — |

While the invention has been particularly shown and described with reference to the preferred embodiment thereof, it will be understood by those skilled in the art that various changes in form and details may be made without departing from the spirit and scope of the invention.

What is claimed is:

1. A method of making a porous biodegradable polymer, comprising the steps of:
   (a) placing a biodegradable polymer and a solvent in a chamber;
   (b) adding a supercritical fluid to the chamber and maintaining the chamber at a predetermined temperature for a sufficient period of time to allow the supercritical fluid to dissolve into the biodegradable polymer with the help of the solvent;
   (c) venting the supercritical fluid and the solvent by reducing the pressure in the chamber, thereby obtaining the porous biodegradable polymer; and
   (d) promptly heating the porous biodegradable polymer to increase the porosity thereof.

2. The method as claimed in claim 1, wherein the biodegradable polymer is a hydrophilic polymer.

3. The method as claimed in claim 1, wherein the biodegradable polymer is selected from the group consisting of gelatin and collagen.

4. The method as claimed in claim 1, wherein the solvent is selected from the group consisting of diluted acidic solutions, diluted basic solutions, neutral solutions, alcohols and mixtures thereof.

5. The method as claimed in claim 1, wherein the supercritical fluid is selected from the group consisting of carbon dioxide, refrigerant, lower hydrocarbons, nitrogen, and ammonia.

6. The method as claimed in claim 1, wherein the supercritical fluid is carbon dioxide.

7. The method as claimed in claim 6, wherein in step (b) the chamber is maintained at a temperature between about 40° to 150° C.

8. The method as claimed in claim 7, wherein in step (b) the chamber is maintained at the predetermined temperature for about 5 minutes to 6 hours.

9. The method as claimed in claim 8, wherein in step (b) the chamber is maintained at a pressure above ambient pressure.

10. The method as claimed in claim 9, wherein step (c) comprises reducing the pressure in the chamber to ambient pressure in a sharp step.

11. The method as claimed in claim 1, further comprising continuously purging the chamber with the supercritical fluid to remove the solvent.

12. The method as claimed in claim 1, wherein the porous biodegradable polymer comprises interconnected pores.

13. The method as claimed in claim 12, wherein the porosity of the porous biodegradable polymer is between about 97% and 99%.

14. The method as claimed in claim 1, wherein the interconnected pores have a diameter between about 50 and 250 µm.

15. The method as claimed in claim 12, wherein the porous biodegradable polymer is used as a three-dimensional scaffold for cell culture.

16. The method as claimed in claim 12, wherein the porous biodegradable polymer is used as a medium for cell and tissue culture.

* * * * *